US012564324B2

(12) United States Patent
Katsumata

(10) Patent No.: US 12,564,324 B2
(45) Date of Patent: Mar. 3, 2026

(54) IMAGE PROCESSING APPARATUS AND IMAGE PROCESSING SYSTEM FOR ABNORMALITY DETECTION

(71) Applicant: TOSHIBA TEC KABUSHIKI KAISHA, Tokyo (JP)

(72) Inventor: Satoshi Katsumata, Sunto Shizuoka (JP)

(73) Assignee: TOSHIBA TEC KABUSHIKI KAISHA, Tokyo (JP)

( * ) Notice: Subject to any disclaimer, the term of this patent is extended or adjusted under 35 U.S.C. 154(b) by 576 days.

(21) Appl. No.: 17/968,823

(22) Filed: Oct. 19, 2022

(65) Prior Publication Data

US 2023/0255490 A1     Aug. 17, 2023

(30) Foreign Application Priority Data

Jan. 18, 2022     (JP) ................................. 2022-005851

(51) Int. Cl.
*G16H 10/60*          (2018.01)
*A61B 5/00*           (2006.01)
*G16H 15/00*          (2018.01)

(52) U.S. Cl.
CPC ................................. *A61B 5/0033* (2013.01)

(58) Field of Classification Search
CPC ........ G16H 15/00; G16H 40/67; G16H 10/60; H04N 1/00209; H04N 1/00281;
(Continued)

(56) References Cited

U.S. PATENT DOCUMENTS 10,219,740 B2 *   3/2019   Warren ................ A61B 5/7275
10,288,418 B2 *   5/2019   Nakazato .................. G06T 7/32
(Continued)

FOREIGN PATENT DOCUMENTS

EP          3591620 A1 *   1/2020   .......... G06K 9/6215
JP          6-238981          8/1994
(Continued)

OTHER PUBLICATIONS

Petrellis, Nikos. "A review of image processing techniques common in human and plant disease diagnosis." Symmetry 10.7 (2018): 270. (Year: 2018).*
(Continued)

*Primary Examiner* — Oneal R Mistry
*Assistant Examiner* — Rachel L Roberts
(74) *Attorney, Agent, or Firm* — Amin, Turocy & Watson, LLP

(57)          ABSTRACT

According to one embodiment, an image processing apparatus includes a format data acquisition unit, a measurement data acquisition unit, a generation unit, and a record processing unit. The format data acquisition unit is configured to acquire format data including a measurement item. The measurement data acquisition unit is configured to acquire measurement data of a biological body relating to the measurement from an electronic apparatus relating to measurement of the measurement item based on communication with the electronic apparatus. The generation unit is configured to generate measurement result data including the measurement item and biological information based on the measurement data. The record processing unit is configured to record the measurement result data.

20 Claims, 5 Drawing Sheets

(58) Field of Classification Search

CPC ........... H04N 1/00352; H04N 1/00798; H04N 1/00278; H04N 1/00307; H04N 1/00315; H04N 1/00326; A61B 5/6898; A61B 5/0033; A61B 5/0022

See application file for complete search history.

(56) References Cited

U.S. PATENT DOCUMENTS

| | | | | |
|---|---|---|---|---|
| 11,490,879 | B2 * | 11/2022 | Ebata .................... | G16H 40/63 |
| 2009/0063612 | A1 * | 3/2009 | Hyo ................... | H04N 1/00204 |
| | | | | 709/201 |
| 2013/0179188 | A1 * | 7/2013 | Hyde .................... | G06Q 10/10 |
| | | | | 705/3 |
| 2013/0225986 | A1 * | 8/2013 | Eggers ................ | A61B 8/0825 |
| | | | | 600/425 |
| 2015/0039336 | A1 * | 2/2015 | Mayer ................ | A61B 5/0059 |
| | | | | 705/2 |
| 2019/0159695 | A1 * | 5/2019 | Kogure ................ | A61B 5/0205 |
| 2019/0279768 | A1 * | 9/2019 | Bates .................... | G16H 50/20 |
| 2020/0244821 | A1 * | 7/2020 | Tanaka .............. | H04N 1/00079 |
| 2021/0057084 | A1 * | 2/2021 | Takeshima ........... | A61B 5/7275 |
| 2021/0319894 | A1 * | 10/2021 | Sobol .................... | G16H 20/30 |
| 2021/0358597 | A1 * | 11/2021 | Minami ................ | G16H 40/67 |
| 2022/0233241 | A1 * | 7/2022 | Shelton, IV ......... | A61B 5/7405 |
| 2023/0023083 | A1 * | 1/2023 | Shelton, IV ....... | A61B 1/00006 |
| 2023/0255490 | A1 * | 8/2023 | Katsumata ........... | A61B 5/0022 |
| | | | | 382/128 |
| 2024/0415611 | A1 * | 12/2024 | Pellissard .............. | A61C 7/002 |

FOREIGN PATENT DOCUMENTS

| | | | | |
|---|---|---|---|---|
| JP | | 2016-54394 | 4/2016 | |
| JP | | 2019-5911 | 1/2019 | |
| WO | WO-2021195616 A1 * | | 9/2021 | ........... A61B 5/7275 |

OTHER PUBLICATIONS

Munir, Mohsin, et al. "DeepAnT: A deep learning approach for unsupervised anomaly detection in time series." Ieee Access 7 (2018): 1991-2005. (Year: 2018).*

Arpaia, P., Crauso, F., De Benedetto, E., Duraccio, L., Improta, G., & Serino, F. (2022). Soft transducer for patient's vitals telemonitoring with deep learning-based personalized anomaly detection. Sensors, 22(2), 536. (Year: 2022).*

Japanese Office Action for Japanese Patent Application No. 2022-005851 dated May 20, 2025.

* cited by examiner

| BODY TEMPERATURE | | _____ |
| BLOOD PRESSURE | SYSTOLIC PHASE | _____ |
| | DIASTOLIC PHASE | _____ |
| HEART RATE | | _____ |
| BLOOD OXYGEN LEVEL | | _____ |
| SLEEP LEVEL | | _____ |
| STRESS LEVEL | | _____ |

FIG. 4

| BODY TEMPERATURE | | 36.5°C |
| BLOOD PRESSURE | SYSTOLIC PHASE | 120mmHg |
| | DIASTOLIC PHASE | 70mmHg |
| HEART RATE | | 65 |
| BLOOD OXYGEN LEVEL | | 98% |
| SLEEP LEVEL | | GOOD |
| STRESS LEVEL | | 30 |

IMAGE PROCESSING APPARATUS AND IMAGE PROCESSING SYSTEM FOR ABNORMALITY DETECTION

CROSS-REFERENCE TO RELATED APPLICATION

This application is based upon and claims the benefit of priority from Japanese Patent Application No. 2022-005851, filed on Jan. 18, 2022, the entire contents of which are incorporated herein by reference.

FIELD

Embodiments described herein relate generally to an image processing apparatus and an image processing system.

BACKGROUND

In an image forming apparatus having a scanner function, a technique of analyzing scanner data and executing a process based on the analyzed data is known.

Incidentally, in general, a format for a test such as a medical check-up is to manually input a measured value. Time and effort is required to manually input a measured value for each item of the format for a test, and an input error or the like may occur.

Accordingly, in the image forming apparatus, a technique of facilitating an input of a measured value in the format for a test is required in consideration of the above-described problem.

DESCRIPTION OF THE DRAWINGS

FIG. 2 is a block diagram schematically illustrating a configuration example of the image forming apparatus;

FIG. 3 is a diagram schematically illustrating one example of a form including measurement items;

FIG. 4 is a diagram schematically illustrating one example of measurement result data;

DETAILED DESCRIPTION

Figure 1:
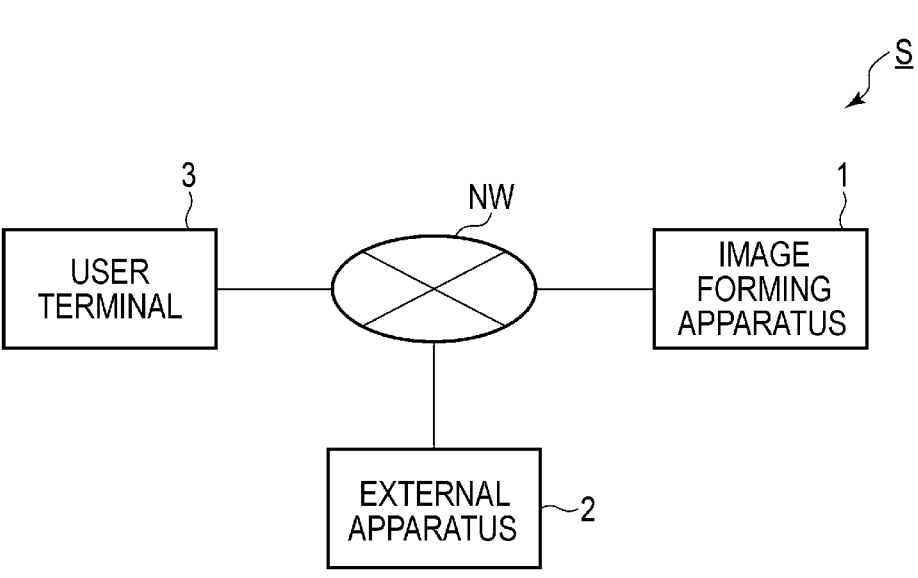
FIG. 1 is a block diagram schematically illustrating a system including an image forming apparatus according to an embodiment.

Embodiments provide a technique capable of generating measurement result data without requiring an input of a user.

In general, according to one embodiment, an image processing apparatus includes a format data acquisition unit, a measurement data acquisition unit, a generation unit, and a record processing unit. The format data acquisition unit is configured to acquire format data including a measurement item. The measurement data acquisition unit is configured to acquire measurement data of a biological body relating to the measurement item from an electronic apparatus relating to measurement of the measurement item based on communication with the electronic apparatus. The generation unit is configured to generate measurement result data including the measurement item and biological information based on the measurement data. The record processing unit is configured to record the measurement result data.

Hereinafter, an embodiment will be described using the drawings. In each of the drawings, the same components are represented by the same reference numerals, and the description thereof will not be repeated.

System Configuration

FIG. 1 is a block diagram schematically illustrating an image processing system S including an image forming apparatus 1 according the embodiment.

The image processing system S includes the image forming apparatus 1, an external apparatus 2, and a user terminal 3. The image forming apparatus 1, the external apparatus 2, and the user terminal 3 are connected to communicate with each other in a wired or wireless manner via a network NW. For example, the network NW includes at least one network among the Internet, a mobile network, and a local area network (LAN). The image processing system S may refer to a system including two apparatuses among the image forming apparatus 1, the external apparatus 2, and the user terminal 3. In the image processing system S, the image forming apparatus 1 acquires a format for a test such as a medical check-up. The image forming apparatus 1 acquires measurement data from the external apparatus 2 corresponding to an unmeasured measurement item in the format for a test. The image forming apparatus 1 executes a process of filling the format for a test with biological information based on the measurement data. The format for a test refers to a form including at least one measurement item relating to a medical check-up or the like. The format for a test may be printed paper or may be data. The format for a test will also be referred to as the form. The measurement item is an item that can be measured by the external apparatus 2. The paper is an example of a sheet.

The image forming apparatus 1 is an electronic apparatus having an electrophotographic printing function. In the following description, it is assumed that the image forming apparatus 1 is a digital multi-functional peripheral (MFP) having a copying function, a print function, a facsimile function, and a scanner function. A configuration example of the image forming apparatus 1 will be described below. The image forming apparatus 1 is an example of the image processing apparatus.

The external apparatus 2 is an electronic apparatus that measures a biological body of a user, acquires measurement data of the biological body, and outputs the measurement data to the image forming apparatus 1. The electronic apparatus includes a computer. The external apparatus 2 can be configured with, for example, a wearable device such as a smart watch or smart glasses, a camera equipped in a smartphone, and a camera in the image forming apparatus 1. The camera measures a biological body of a user. The external apparatus 2 may be configured with a sensor that can acquire biological data, for example, a vital sensor, a temperature sensor, a humidity sensor, a pressure sensor, an optical sensor, a sound sensor, a human detection sensor, a vibration sensor, a current sensor, a voltage sensor, a position sensor, a switch sensor, or a gyrosensor. The biological data is an example of the measurement data. The sensor measures a biological body of a user. The external apparatus 2 may be one kind or a combination of a plurality of kinds among the external apparatuses described above. The external apparatus 2 includes a control unit, a communication circuit, and an input and output interface that are the same as a control unit 10, a communication circuit 40, and an input and output interface 50 described below in the image forming apparatus 1. The control unit includes a control circuit, a main memory, and a storage that are the same as a control circuit 11, a main memory 12, and a storage 13 described below in the image forming apparatus 1. The control circuit loads programs stored in advance in the main memory or the storage to the main memory. The control circuit executes various operations by executing the programs loaded to the main memory. The control circuit acquires measurement data of a biological body, and outputs the acquired measurement data to the image forming apparatus 1 via the network NW. The control circuit may output the acquired measurement data to the user terminal 3 via the network NW. The communication circuit is an interface that connects the external apparatus 2 and an apparatus such as the image forming apparatus 1 to each other via the network NW to be capable of communication therebetween. The input and output interface is an interface that connects the external apparatus 2 and the apparatus such as the image forming apparatus 1 by wired connection. The external apparatus 2 is an example of a sensing device that acquires measurement data.

The user terminal 3 is an electronic apparatus capable of information processing. For example, the user terminal 3 is a personal computer (PC), a tablet terminal, or a smartphone but is not limited thereto. The user terminal 3 transmits print data to the image forming apparatus 1. The print data is data regarding a job relating to printing that is requested from the user terminal 3 to the image forming apparatus 1. The print data includes print settings input from the user through the user terminal 3. The print settings include various settings relating to printing, for example, a color mode, a paper type, a printing mode, the number of sheets to be printed, or a paper size. The paper is an example of a medium. The print data includes print target data designated by the user through the user terminal 3. The print data includes identification information of the user.

Apparatus Configuration

Figure 2:
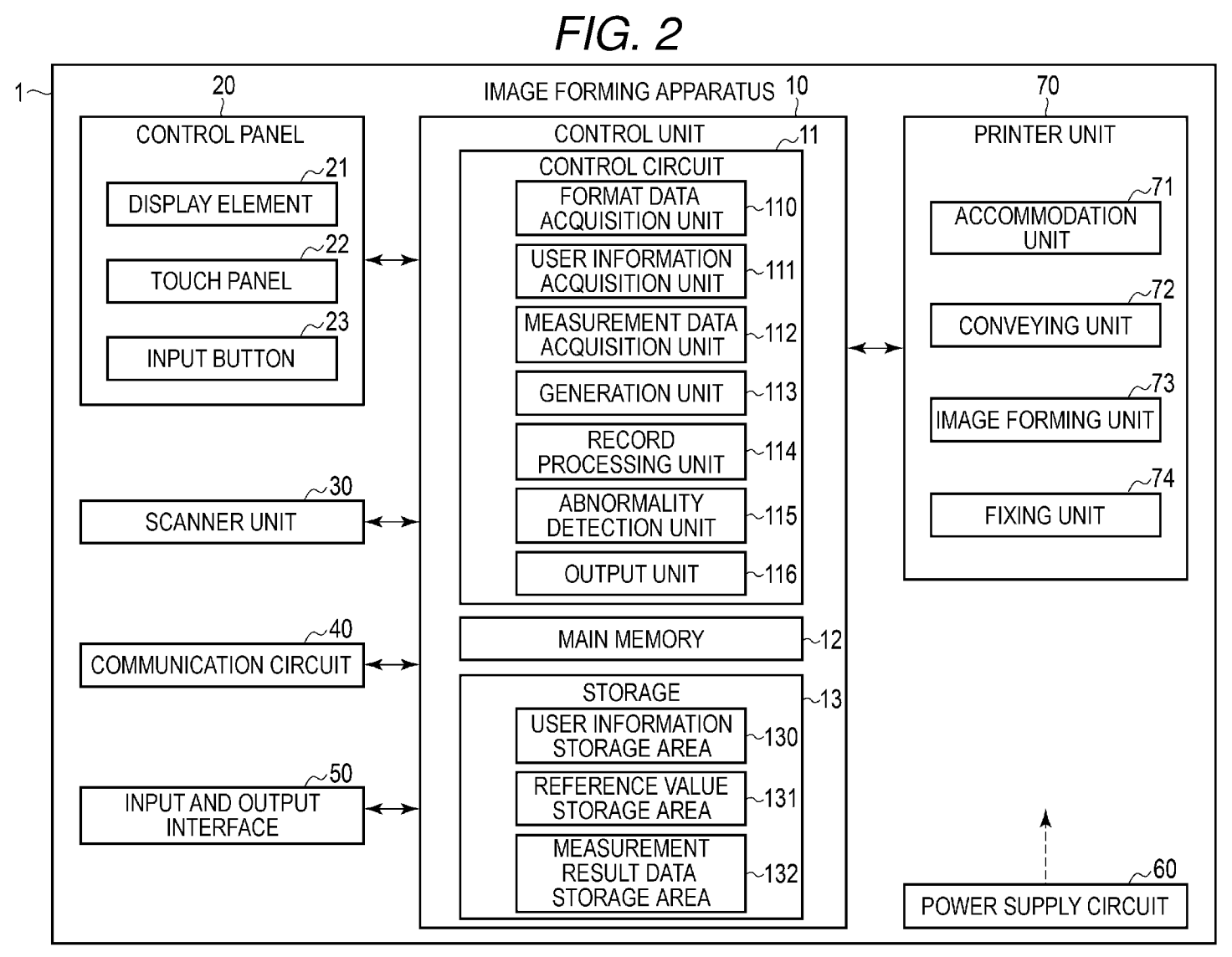

FIG. 2 is a block diagram schematically illustrating a configuration example of the image forming apparatus 1 according to the embodiment.

The image forming apparatus 1 includes the control unit 10, a control panel 20, a scanner unit 30, the communication circuit 40, the input and output interface 50, a power supply circuit 60, and a printer unit 70.

The control unit 10 controls operations of the various units in the image forming apparatus 1. The control unit 10 includes the control circuit 11, the main memory 12, and the storage 13. The control unit 10 configures a computer of the image forming apparatus 1.

The control circuit 11 corresponds to a central part of the image forming apparatus 1. The control circuit 11 includes a processor such as a central processing unit (CPU). In addition to or instead of the CPU, the control circuit 11 may include an application specific integrated circuit (ASIC), a field-programmable gate array (FPGA), or a graphics processing unit (GPU). The control circuit 11 loads programs stored in advance in the main memory 12 or the storage 13 to the main memory 12. The control circuit 11 executes various operations by executing the programs loaded to the main memory 12.

The main memory 12 corresponds to a main memory part of the image forming apparatus 1. The main memory 12 includes a nonvolatile memory area and a volatile memory area. The main memory 12 stores an operating system or a program in the nonvolatile memory area. The main memory 12 uses the volatile memory area as a work area where data is appropriately rewritten by the control circuit 11. For example, the main memory 12 includes a read only memory (ROM) as the nonvolatile memory area. For example, the main memory 12 includes a random access memory (RAM) as the volatile memory area.

The storage 13 corresponds to an auxiliary storage part of the image forming apparatus 1. For example, the storage 13 includes a hard disk drive (HDD). In addition to or instead of the HDD, the storage 13 may include a semiconductor storage medium such as a solid state drive (SSD). The storage 13 stores the above-described programs, data used for the control circuit 11 to execute various processes, and data generated during the processes of the control circuit 11. The storage 13 may store print data.

The storage 13 includes a user information storage area 130. The user information storage area 130 stores user information of each user. The user information includes user identification information, user attribute information, identification information of the user terminal 3 that is used by the user, identification information of the external apparatus 2 that is used by the user, a biological information history of the user, information representing whether or not an abnormal value notification is necessary, and information regarding a notification destination to which the abnormal value is notified. The user identification information is unique identification information that is assigned to each user to identify the user. The user attribute information includes information such as a gender or an age. The identification information of the user terminal 3 is unique identification information that is assigned to each user terminal 3 to identify the user terminal 3. The identification information of the user terminal 3 includes an IP address of the user terminal 3. The identification information of the external apparatus 2 is unique identification information that is assigned to each external apparatus 2 to identify the external apparatus 2. The identification information of the external apparatus 2 includes an IP address of the external apparatus 2. The biological information history represents a record of a history of previous biological information based on the measurement data that is previously acquired by the external apparatus 2. The biological information is information generated based on the measurement data acquired by the external apparatus 2. The biological information is, for example, information where the measurement data is generated in accordance with a measurement unit or a measurement level of each measurement item. Examples of the measurement unit include "° C.", "mmHg", and "%" depending on the measurement items. Examples of the measurement level include "good, normal, and bad" and "high, middle, and low" depending on the measurement items. In the following description, "generation" may be replaced with "conversion".

The information representing whether or not an abnormal value notification is necessary includes information representing whether or not to execute predetermined notification if the biological information based on the measurement data acquired by the external apparatus 2 represents an abnormal value. The abnormal value is a value determined based on a degree of discrepancy from a reference value of the measurement item. In the following description, it is assumed that "value" includes a numerical value and a level. The abnormal value may be, for example, a value exceeding the reference value or a value falling below the reference value. For example, a case where the measurement item is a blood pressure will be described. If the reference value in a systolic phase of the blood pressure is 129 or less, the abnormal value is a value exceeding 129. The abnormal value may be, for example, a value exceeding the reference value by a predetermined range or a value falling below the reference value by a predetermined range. For example, a case where the measurement item is a stress level will be described. If the reference value of the stress level is 50 or less and the predetermined range is "the reference value plus 10", the abnormal value is a value exceeding 60. The abnormal value may be a value determined based on a degree of discrepancy from biological information at a previous time point based on the biological information history of the user.

The information regarding the notification destination of the abnormal value includes a mail address and a fax number of a notification destination institution to which the abnormal value is notified. The notification destination institution includes a medical institution relating to a contact person designated by the user or the measurement item.

The storage 13 includes a reference value storage area 131. The reference value storage area 131 stores the reference value correlated with the measurement item. The reference value is a value for determining a normal value or an abnormal value set for each measurement item. The reference value may be a predetermined value or may be a value representing a predetermined range. Examples of the reference value include a value such as "XX or more", "YY or less", or "XXX to YYY".

The storage 13 includes a measurement result data storage area 132. The measurement result data storage area 132 stores measurement result data including the measurement item and biological information based on the measurement data.

The measurement result data is data representing the biological information for each measurement item. The measurement result data may be, for example, a table where a numerical value, a level, or the like represented by the biological information for each measurement item is shown. The measurement result data may include time-series data of biological information described below. The measurement result data may include a graph illustrating the biological information for each measurement item as the time-series data. The measurement result data may include both of the table and the graph. The measurement result data may include abnormality information representing an abnormality of the biological information.

The control panel 20 includes a display element 21, a touch panel 22, and an input button 23.

The display element 21 displays an image. The display element 21 is, for example, a liquid crystal display or an organic electroluminescence (EL) display and is not limited thereto. The touch panel 22 is a device that forms a touch screen together with the display element 21 by being stacked on the display element 21. The touch panel 22 detects a touch of the user on the display element 21. The touch panel 22 is an example of an input interface that inputs an instruction of the user. The input button 23 is a pressable button such as a print start button. The input button 23 is an example of an input interface that inputs an instruction of the user.

The scanner unit 30 is a device that reads a character or an image such as a diagram or a picture that is drawn on paper placed at a predetermined position. The scanner unit 30 includes a line sensor. The line sensor may be a charge coupled device (CCD) type. The line sensor may be a contact image sensor (CIS) type. The scanner unit 30 generates image data based on the image read using the line sensor. The scanner unit 30 transmits the generated image data to the control unit 10. The control unit 10 stores the received image data in the storage 13 or transmits the received image data to the printer unit 70.

The communication circuit 40 is an interface for communication of the image forming apparatus 1 with an external apparatus. The communication circuit 40 connects the image forming apparatus 1 and the user terminal 3 so as to communicate with each other via the network NW. The communication circuit 40 connects the image forming apparatus 1 and the external apparatus 2 so as to communicate with each other via the network NW.

The input and output interface 50 is an interface that connects the external apparatus 2 mounted on the image forming apparatus 1. The input and output interface 50 includes a connector of a cable that connects the image forming apparatus 1 and the external apparatus 2.

The power supply circuit 60 converts an alternating current power supplied from a commercial power supply into a direct current power and supplies the power to the respective units of the image forming apparatus 1. The power supply circuit 60 can be controlled by the control circuit 11.

The printer unit 70 is a unit that forms an image on paper. For example, the printer unit 70 forms an image on paper based on the image data generated by the scanner unit 30 or the print data transmitted from the user terminal 3 via the network NW. The printer unit 70 forms a measurement result image based on the measurement result data on paper based on the measurement result data. Here, an example of the printer unit 70 using a tandem type toner image transfer unit will be described. The printer unit 70 includes an accommodation unit 71, a conveying unit 72, an image forming unit 73, and a fixing unit 74.

The accommodation unit 71 accommodates paper. The accommodation unit 71 includes a paper feed cassette and a pickup roller. The paper feed cassette accommodates paper. The pickup roller picks up paper from the paper feed cassette one by one. The pickup roller supplies the picked paper to the conveying unit 72.

The conveying unit 72 conveys paper in the printer unit 70. The conveying unit 72 includes a plurality of rollers and a registration roller. The plurality of rollers include a roller that conveys the paper supplied by the pickup roller to the registration roller. The plurality of rollers include a roller that is provided downstream of the fixing unit 74 described below and discharges the paper to a paper discharge unit. The registration roller conveys the paper to a transfer unit of the image forming unit 73 described below at a timing where the transfer unit transfers a toner image to the paper.

The image forming unit 73 forms the toner image on the paper. The image forming unit 73 includes an intermediate transfer belt, a plurality of developing units, an exposure unit, and the transfer unit.

The intermediate transfer belt is an endless belt. The plurality of developing units correspond to the number of types of toners. The plurality of developing units include a developing unit for black, a developing unit for cyan, a developing unit for magenta, and a developing unit for yellow. Each of the developing units includes a photoconductive drum. Each of the developing units includes a charging unit, a developing device, a primary transfer roller, a cleaning unit, and a charge eraser that are provided in the vicinity of the photoconductive drum. The photoconductive drum includes a photoreceptor layer on a surface. The charging unit uniformly charges the photoreceptor layer on the surface of the photoconductive drum. The developing device develops an electrostatic latent image on the surface of the photoconductive drum with the toner. The developing device forms a toner image on the surface of the photoconductive drum. The primary transfer roller faces the photoconductive drum, and the intermediate transfer belt is interposed between the primary transfer roller and the photoconductive drum. The primary transfer roller transfers the toner image on the surface of the photoconductive drum to the intermediate transfer belt. The cleaning unit removes the toner that remains on the surface of the photoconductive drum without being transferred. The charge eraser irradiates the surface of the photoconductive drum with light. The charge eraser irradiates the photoreceptor layer of the photoconductive drum with light to erase charge.

The exposure unit irradiates the surface of the photoconductive drum of each of the developing units with laser light through an optical system such as a polygon mirror. The exposure unit forms an electrostatic pattern on the surface of the photoconductive drum as the electrostatic latent image.

The transfer unit transfers the toner image charged on the surface of the intermediate transfer belt to paper. The transfer unit includes a support roller and a secondary transfer roller that are configured such that the intermediate transfer belt and the paper are interposed therebetween from both sides in a thickness direction.

The fixing unit 74 applies heat and pressure to the paper on which the toner image supplied from the image forming unit 73 is formed. The fixing unit 74 fixes the formed toner image to the paper using the heat and pressure.

The hardware configuration of the image forming apparatus 1 is not limited to the configuration described above. For the image forming apparatus 1, the components described above can be removed or modified and a new component can be added.

Each of the units implemented by the control circuit 11 described above will be described.

The control circuit 11 implements a format data acquisition unit 110, a user information acquisition unit 111, a measurement data acquisition unit 112, a generation unit 113, a record processing unit 114, an abnormality detection unit 115, and an output unit 116. Each of the units implemented by the control circuit 11 will also be referred to as each of the functions. Each of the units being implemented by the control circuit 11 can also be implemented by a control unit including the control circuit 11 and the main memory 12.

The format data acquisition unit 110 acquires format data such as the format for a test including the measurement items. The format data includes image data of the format for a test or text data of the format for a test. The format data acquisition unit 110 may acquire the format data generated through the scanner unit 30 or may acquire the format data as the print target data from the user terminal 3. In the following description, "acquisition" may be replaced with "reception".

The format data acquisition unit 110 analyzes the acquired format data and acquires the measurement item in the format data. The format data acquisition unit 110 determines whether or not an unmeasured measurement item is present in the measurement items. The unmeasured measurement item refers to a measurement item where the biological information is not recorded. The unmeasured measurement item will also be referred to as the unmeasured item.

The user information acquisition unit 111 acquires the user information from the user information storage area 130. The user information acquisition unit 111 may identify the user from the information in the format data acquired by the format data acquisition unit 110. The user information acquisition unit 111 may acquire the user identification information to identify the user using a contactless card reader or the like in the image forming apparatus 1. The user identification information is information based on which each user can be identified. The user identification information is used for allowing the image forming apparatus 1 to authenticate the user. The user information acquisition unit 111 acquires the user information correlated with the user identification information from the user information storage area 130 based on the acquired user identification information.

The measurement data acquisition unit 112 acquires the measurement data of the user from the external apparatus 2 relating to the measurement of the measurement item via the communication circuit 40 or the input and output interface 50. The measurement data acquisition unit 112 acquires the measurement data based on the unmeasured item in the format data acquired by the format data acquisition unit 110. The measurement data acquisition unit 112 selects the external apparatus 2 relating to the unmeasured item based on the user information, and acquires the measurement data from the selected external apparatus 2. The measurement data acquisition unit 112 may acquire the measurement data from the external apparatus 2 previously correlated with the measurement item. If the external apparatus 2 is a camera, the external apparatus 2 images a change in skin color or a vital sign such as a lung movement. In this case, the measurement data includes a measurement result such as a body temperature, a heart rate, a respiration rate, a consciousness level, or face color information. If the external apparatus 2 is a wearable device, the external apparatus 2 measures a body height, a body weight, a blood pressure, a heart rate, or the like. In this case, the measurement data includes a measurement result such as a body height, a body weight, a heart rate, a blood pressure, or a sleep level. The measurement data acquisition unit 112 may access the external apparatus 2 on a regular basis to acquire the measurement data.

The generation unit 113 generates biological information based on the measurement data. The generation unit 113 generates time-series data of biological information based on the biological information history of the user in the user information and biological information based on newly acquired measurement data. The biological information based on the newly acquired measurement data will also be referred to as the current biological information. The time-series data may also be data where the previous biological information and the current biological information are arranged in a time-series manner and displayed. The time-series data may be a graph illustrating biological information generated from the previous biological information and the current biological information. The time-series data may include a measurement date of the measurement data. The time-series data may include a comparison result between the latest biological information and the current biological information. The time-series data may be generated as data in any display manner.

The generation unit 113 generates measurement result data including the measurement item and the biological information. The generation unit 113 may generate measurement result data including the time-series data. The generation unit 113 may generate measurement result data including the abnormality information. The generation unit 113 may generate image data representing the measurement result as the measurement result data.

The record processing unit 114 records the measurement result data. The record processing unit 114 may control the printer unit 70 to print the measurement result data as the record of the measurement result data. The record processing unit 114 may store the measurement result data in the measurement result data storage area 132 of the storage 13 as the record of the measurement result data.

The abnormality detection unit 115 detects an abnormality of the current biological information based on the reference value of the biological information. The abnormality detection unit 115 acquires the reference value of the biological information of each measurement item from the reference value storage area 131. The abnormality detection unit 115 compares the reference value of the biological information of each measurement item and the current biological information to each other to detect the abnormal value. The abnormality detection unit 115 may detect the abnormal value based on the biological information history of the user. The abnormality detection unit 115 determines whether or not a notification of the abnormal value is necessary based on the user information.

The output unit 116 outputs the notification of the abnormal value based on the determination result of whether or not the notification of the abnormal value is necessary by the abnormality detection unit 115. The output unit 116 outputs the notification of the abnormal value to the notification destination institution based on the user information. The output unit 116 may output the notification of the abnormal value and the time-series data of the biological information to the notification destination institution. In the following description, "output" may be replaced with "transmit".

The format for a test including the measurement items will be described.

FIG. 3 is a diagram schematically illustrating one example of the form including measurement items according to the embodiment.

The format for a test illustrated in FIG. 3 is a form including a plurality of measurement items used in a medical check-up. Examples of the measurement items include a body temperature, a blood pressure, a heart rate, a blood oxygen level, a sleep level, and a stress level. In the format for a test illustrated in FIG. 3, all of the measurement items are empty. The empty measurement items represent unmeasured items where the measurement data is not recorded.

The measurement result data will be described.

FIG. 4 is a diagram schematically illustrating one example of the measurement result data according to the embodiment.

The measurement result data illustrated in FIG. 4 is an example of data where the measurement data is acquired and the biological information is recorded in the format for a test illustrated in FIG. 3. For example, for the measurement items of the body temperature, the blood pressure, the heart rate, and the blood oxygen level, information where the measurement result represented by the measurement data is generated in accordance with the measurement unit of each of the measurement items is recorded. For the measurement items of the sleep level and the stress level, information where the measurement result represented by the measurement data is generated in accordance with the measurement level of each of the measurement items is recorded. For the measurement item "sleep level", for example, the measurement result represented by the measurement data is classified into any one of "good, normal, and bad", and the classification result is recorded as the biological information. For the measurement item "stress level", for example, the measurement result represented by the measurement data is classified into any one of "high, middle, and low", and the classification result is recorded as the biological information. The measurement result represented by the measurement data may be classified based on a preset value or may be classified using a well-known method.

Figure 5:
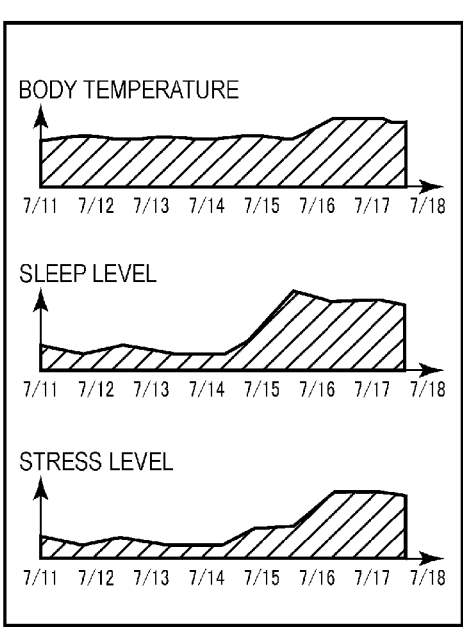
FIG. 5 is a diagram schematically illustrating another example of the measurement result data.

FIG. 5 is a diagram schematically illustrating another example of the measurement result data according to the embodiment.

The measurement result data illustrated in FIG. 5 is another example of the image where the measurement data is acquired and the biological information is recorded in the format for a test illustrated in FIG. 3. The measurement result data illustrated in FIG. 5 is a graph illustrating the time-series data of the biological information for each of the measurement items. FIG. 5 illustrates the graph that is generated based on biological information based on measurement data of one user acquired from July 11 to July 18 for the measurement items "body temperature", "sleep level", and "stress level". The graph may be generated for all of the measurement items or may be generated for measurement items that are preset by the user, a manager, or the like. The graph may also be generated for a measurement item of biological information for which an abnormality is detected. The user can visually recognize the measurement results by the graph display.

A procedure of the process by the image processing system S will be described.

In the following process, the user of the image forming apparatus 1 scans the format for a test of a medical check-up shown in FIG. 3 through the scanner unit 30. The image processing system S executes the following process if the format for a test is scanned by the user. The data of the format for a test of the medical check-up may be output to the image forming apparatus 1 through the user terminal 3 used by the user. In this case, the image processing system S executes the following process if the data of the format for a test is output to the image forming apparatus 1 by the user.

Figure 6:
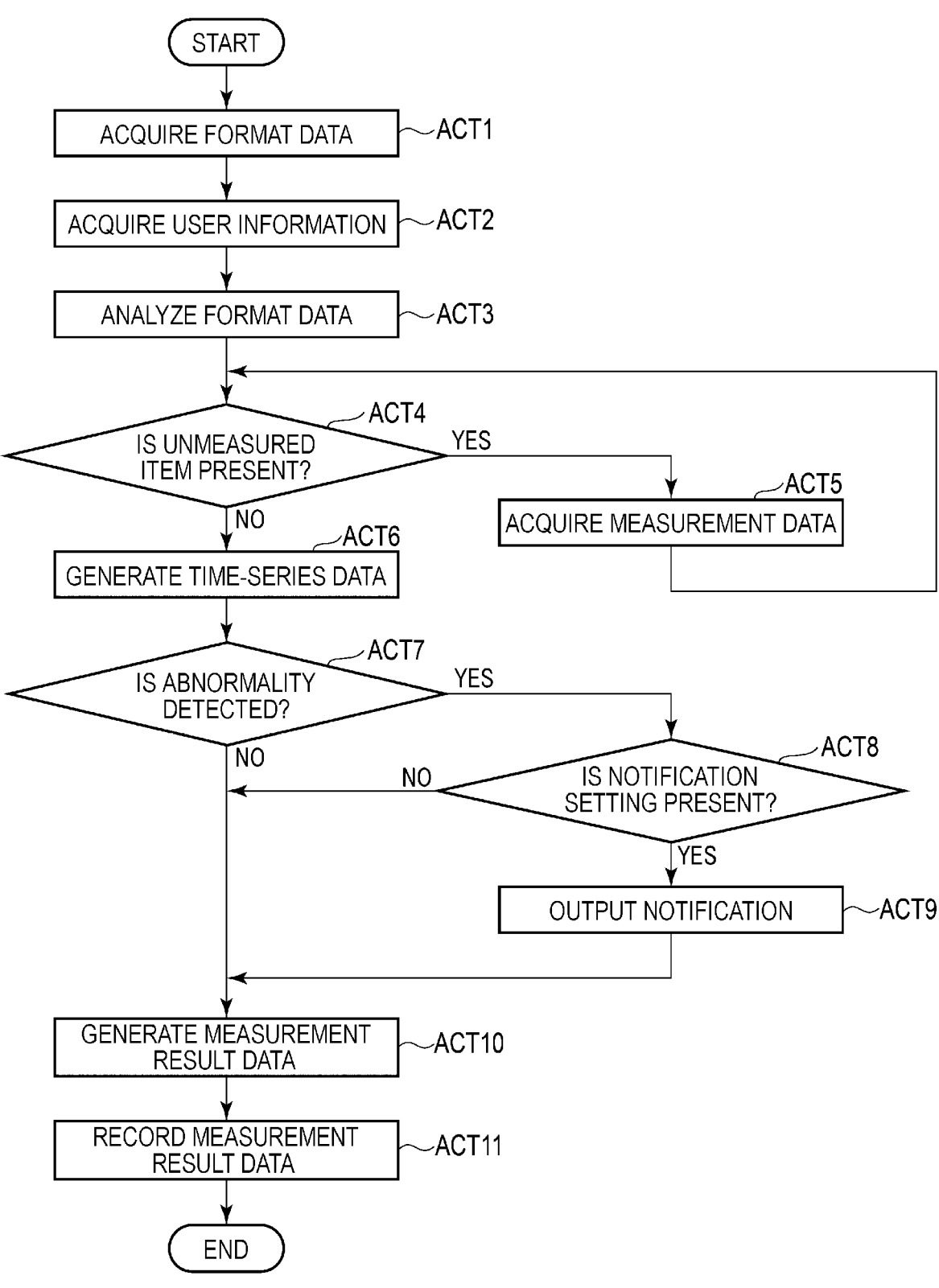
FIG. 6 is a flowchart illustrating a procedure of an image processing operation in the image forming apparatus.

FIG. 6 is a flowchart illustrating the procedure of the image processing operation in the image forming apparatus 1 according to the embodiment.

The procedure described below is merely exemplary and may be changed as long as each of the processes can be executed. In addition, in the procedure described below, steps can be omitted, replaced, and added depending on embodiments.

The format data acquisition unit 110 acquires format data such as the format for a test including the measurement items (ACT 1). In ACT 1, for example, the format data acquisition unit 110 acquires the format data generated through the scanner unit 30. In this case, the format data acquisition unit 110 acquires the image data of the format for a test. The format data acquisition unit 110 may acquire the format data as the print target data in the print data output through the user terminal 3. In this case, the format data acquisition unit 110 acquires text data or image data of the format for a test.

The user information acquisition unit 111 acquires the user information from the user information storage area 130 (ACT 2). In ACT 2, for example, the user information acquisition unit 111 identifies the user based on the format data. If the print data includes the format data, the user information acquisition unit 111 may identify the user based on the user identification information in the print data. The user information acquisition unit 111 may identify the user based on the user identification information correlated with the format data. The user identification information correlated with the format data includes, for example, the identification information of the user terminal 3. The user information acquisition unit 111 acquires the user identification information to identify the user using a contactless card reader or the like in the image forming apparatus 1. The user information acquisition unit 111 acquires the user information correlated with the identified user from the user information storage area 130.

The format data acquisition unit 110 analyzes the format data (ACT 3). In ACT 3, for example, if the format data is image data, the format data acquisition unit 110 analyzes the image data by optical character recognition (OCR) or the like. The format data acquisition unit 110 acquires the measurement item using keyword search or the like based on the analyzed data. If the format data is text data, the format data acquisition unit 110 acquires the measurement item using a keyword or the like in the text data. The format data acquisition unit 110 may acquire the measurement item based on the format data previously registered in the image forming apparatus 1. As a method of acquiring the measurement item, a well-known technique may be used.

The format data acquisition unit 110 determines whether or not an unmeasured item is present in the measurement items (ACT 4). In ACT 4, for example, the format data acquisition unit 110 determines whether or not the biological information is recorded in the biological information input field corresponding to the measurement item. The measurement item for which the biological information is not recorded in the biological information input field is an example of the unmeasured item. If the format data acquisition unit 110 determines that the unmeasured item is present (ACT 4: YES), the process proceeds from ACT 4 to ACT 5. If the format data acquisition unit 110 determines that the unmeasured item is not present (ACT 4: NO), the process proceeds from ACT 4 to ACT 6.

The measurement data acquisition unit 112 acquire measurement data of a biological body relating to the measurement item from the external apparatus 2 relating to measurement of the measurement item based on communication with the external apparatus 2 (ACT 5). In ACT 5, for example, the measurement data acquisition unit 112 acquires the unmeasured item. The measurement data acquisition unit 112 accesses at least one external apparatus 2 correlated with the unmeasured item based on the user information. The measurement data acquisition unit 112 outputs a measurement data acquisition instruction to the external apparatus 2. The measurement data acquisition instruction includes, for example, an instruction such as a start-up instruction of the external apparatus 2, an imaging instruction, or a measurement instruction. The measurement data acquisition unit 112 acquires the measurement data of the user from the external apparatus 2. The measurement data acquisition unit 112 may acquire the measurement data from the external apparatus 2 previously correlated with the measurement item irrespective of the user information. The measurement data acquisition unit 112 may acquire the measurement data from a plurality of different external apparatuses 2. In this case, the measurement data can be collectively collected from the plurality of external apparatuses 2 and recorded.

The generation unit 113 generates time-series data based on the biological information history in the user information and the biological information (ACT 6). In ACT 6, for example, the generation unit 113 generates the current biological information based on the measurement data. The generation unit 113 acquires the biological information history from the user information. The generation unit 113 generates the time-series data based on the biological information history and the generated current biological information.

The abnormality detection unit 115 detects an abnormality of the biological information based on the measurement data based on the reference value of the biological information (ACT 7). In ACT 7, for example, the abnormality detection unit 115 acquires the reference value of the biological information of each unmeasured item from the reference value storage area 131. The abnormality detection unit 115 determines whether or not the current biological information represents the abnormal value based on the reference value of the biological information of each unmeasured item and the current biological information. The determination that the current biological information represents the abnormal value is an example of the detection of the abnormality of the biological information.

For example, the abnormality detection unit 115 compares the reference value of the biological information of each unmeasured item and the current biological information to each other. If the current biological information represents a value exceeding the reference value or a value falling below the reference value, the abnormality detection unit 115 detects an abnormality of the biological information. In another example, if the current biological information represents a value exceeding the reference value by a predetermined range or a value falling below the reference value by a predetermined range, the abnormality detection unit 115 may detect an abnormality of the biological information. The predetermined range may be a preset range or may be a range that is appropriately set by a manager or the like.

The abnormality detection unit 115 may detect an abnormality of the biological information based on a degree of discrepancy from biological information at a previous time point based on the biological information history of the user. In this case, the abnormality detection unit 115 acquires the biological information history of each unmeasured item of the user from the user information. The abnormality detection unit 115 compares the biological information at the previous time point of each unmeasured item and the current biological information to each other. If the degree of discrepancy between the biological information at the previous time point of each unmeasured item and the current biological information exceeds a predetermined value, the abnormality detection unit 115 detects an abnormality of the biological information. The predetermined value may be a preset range or may be a range that is appropriately set by a manager or the like. The biological information at the previous time point may be the latest biological information or the average value of biological information at a plurality of previous time points.

The abnormality detection unit 115 may detect an abnormality of the biological information for all of the measurement items in the format for a test. In this case, the current biological information may include biological information recorded in the format for a test and biological information based on newly measured measurement data. The abnormality detection unit 115 acquires the reference value of the biological information for all of the measurement items. The abnormality detection unit 115 determines whether or not the current biological information represents the abnormal value based on the reference value of the biological information of each measurement item and the current biological information. The abnormality detection unit 115 may acquire the biological information history of each measurement item of the user from the user information. The abnormality detection unit 115 may compare the biological information at the previous time point of each measurement item and the current biological information to each other to detect an abnormality of the biological information.

If the abnormality of the biological information is detected by the abnormality detection unit 115 (ACT 7:

YES), the process proceeds from ACT 7 to ACT 8. If the abnormality of the biological information is not detected by the abnormality detection unit 115 (ACT 7: NO), the process proceeds from ACT 7 to ACT 10.

The abnormality detection unit 115 determines whether or not a notification of the abnormal value is necessary based on the user information (ACT 8). In ACT 8, for example, the abnormality detection unit 115 acquires information representing whether or not an abnormal value notification is necessary from the user information. If the abnormality detection unit 115 determines that the abnormal value notification is present (ACT 8: YES), the process proceeds from ACT 8 to ACT 9. If the abnormality detection unit 115 determines that the abnormal value notification is not present (ACT 8: NO), the process proceeds from ACT 8 to ACT 10.

The output unit 116 outputs the notification of the abnormal value based on the determination result of whether or not the notification of the abnormal value is necessary in response to the detection of the abnormality by the abnormality detection unit 115 (ACT 9). In ACT 9, for example, if the determination result of whether or not the notification of the abnormal value is necessary by the abnormality detection unit 115 is that the abnormal value notification is present, the output unit 116 acquires information regarding the notification destination institution based on the user information. The output unit 116 outputs the notification of the abnormal value to the notification destination institution. In one example, the output unit 116 outputs the notification of the abnormal value to the mail address of the notification destination institution. In another example, the output unit 116 outputs the notification of the abnormal value to the fax number of the notification destination institution. The output unit 116 may output the biological information of the user or the time-series data together with the notification of the abnormal value. The output unit 116 may control the printer unit 70 to print the notification of the abnormal value. In the following description, "in response to" may be replaced with "based on".

The generation unit 113 generate measurement result data including the measurement item and biological information based on the measurement data (ACT 10). In ACT 10, for example, the generation unit 113 generates the measurement result data where the current biological information is correlated with each measurement item. The generation unit 113 may generate measurement result data including the time-series data. The generation unit 113 may generate measurement result data including the abnormality information representing the abnormality of the biological information. The generation unit 113 may generate the measurement result data in any form such as text data, graph data, or image data. The abnormality information is information representing the abnormal value in an identifiable manner. The abnormality information may be data in any display manner, for example, text data, an icon, a symbol, or an image.

The record processing unit 114 records the measurement result data (ACT 11). In one example, the record processing unit 114 controls the printer unit 70 to print the measurement result data. In another example, the record processing unit 114 stores the measurement result data in the measurement result data storage area 132 of the storage 13.

The example where the generation unit 113 generates the time-series data is described above. However, the embodiment is not limited to this example. The generation unit 113 does not need to generate the time-series data. In this example, the generation unit 113 does not execute the process of ACT 6.

In the above-described embodiment, the test format of the medical check-up is described as an example. However, the embodiment is not limited to this example. The embodiment is applicable to various formats including measurement items that can be measured by the external apparatus 2. The various formats include, for example, a format for checking an apparatus.

Effects

The image processing apparatus according to the embodiment acquires format data including a measurement item. The image processing apparatus acquires measurement data of a biological body relating to the measurement item from an electronic apparatus relating to measurement of the measurement item based on communication with the electronic apparatus. The image processing apparatus generates measurement result data including the measurement item and biological information based on the measurement data. The image processing apparatus records the measurement result data.

As a result, the image processing apparatus can acquire the measurement data from the electronic apparatus for the measurement item in the format data and can record the measurement data. Therefore, the image processing apparatus can generate the measurement result data without requiring an input of a user. This way, the image processing apparatus can save time and effort for an input of measurement data and can generate the measurement result data without an input error.

The image processing apparatus according to the embodiment acquires user information including a biological information history. The image processing apparatus generates time-series data of biological information based on the biological information history in the user information and the biological information. The measurement result data includes the time-series data.

As a result, the image processing apparatus can provide the history of the measurement result for each user to the user. Therefore, the user can visually recognize a variation in the measurement result. This way, the image processing apparatus provides the history of the measurement result to the user such that the measurement result data that can urge the user to recognize a change in the measurement result can be generated.

The image processing apparatus according to the embodiment detects an abnormality of the biological information based on the measurement data, based on a reference value of biological information. The image processing apparatus outputs a notification in response to the detection of the abnormality.

As a result, the image processing apparatus can notify the abnormality instantaneously. Therefore, the image processing apparatus can take an appropriate action timely for the abnormality of the measurement result. This way, the image processing apparatus can notify the abnormality based on a setting of the user to urge the user to recognize a change in the measurement result.

The image processing apparatus according to the embodiment generates the measurement result data that includes abnormality information representing the abnormality.

This way, the image processing apparatus can generate the measurement result data that can urge the user to recognize a change in the measurement result.

The image processing apparatus may be implemented by one apparatus as in the image forming apparatus 1 or may be implemented by a plurality of apparatuses where the functions are distributed.

The program may be transferred in a state where the program is stored in an electronic apparatus or may be transferred in a state where the program is not stored in an electronic apparatus. In the latter case, the program may be transferred via a network or may be transferred in a state where the program is recorded in a recording medium. The recording medium is a non-transitory tangible medium. The recording medium is a computer-readable medium. The form of the recording medium is not limited as long as it is a medium such as a CD-ROM or a memory card that can store the program and can be read by a computer.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such embodiments or modifications as would fall within the scope and spirit of the inventions.

What is claimed is:

1. An image processing apparatus, comprising:
a format data acquisition component configured to acquire format data including a plurality of measurement items;
a measurement data acquisition component configured to acquire measurement data of a biological body relating to the plurality of measurement items from one or more electronic apparatuses relating to measurement of the plurality of measurement items based on communication with the electronic apparatuses;
a generation component configured to generate first measurement result data including the plurality of measurement items and including first biological information based on the measurement data, and configured to generate second measurement result data including the plurality of measurement items and including second biological information based on the measurement data, the second biological information being at least partially different than the first biological information,
wherein the generation component is further configured to classify, based on user information corresponding to the biological body, the first measurement result data using a first set of specified hierarchy-based classes and to classify, based on the user information, the second measurement result data using a second set of specified hierarchy-based classes that are different form the first set of specified hierarchy-based classes; and
a record processing component configured to record the first measurement result data and the second measurement result data.

2. The image processing apparatus according to claim 1, further comprising a user information acquisition component configured to acquire the user information including a biological information history,
wherein the generation component generates time-series data of biological information based on the biological information history in the user information and the biological information, and
the measurement result data includes the time-series data.

3. The image processing apparatus according to claim 1, further comprising:

an abnormality detection component configured to detect a plurality of different abnormalities of the biological information based on reference values of biological information; and
an output component configured to output a set of notifications in response to the detection of the abnormalities by the abnormality detection component,
wherein the output component outputs a first notification, of the set of notifications, to a first destination institution and a second notification, of the set of notifications, to a second destination institution that is different from the first destination institution.

4. The image processing apparatus according to claim 3, wherein the measurement result data includes abnormality information representing the abnormality.

5. The image processing apparatus according to claim 1, wherein the electronic apparatus comprises a sensor configured to acquire biological data.

6. The image processing apparatus according to claim 1, wherein the measurement item is a medical measurement item.

7. The image processing apparatus according to claim 1, wherein the measurement data acquisition component communicates wirelessly with the electronic apparatus.

8. The image processing apparatus according to claim 3, wherein the abnormality comprises a value exceeding a reference value by a predetermined range or a value falling below the reference value by the predetermined range.

9. An image processing system comprising one or more electronic apparatuses and an image processing apparatus,
wherein the electronic apparatus acquires measurement data of a biological body and outputs the measurement data to the image processing apparatus, and
the image processing apparatus comprises:
a format data acquisition component configured to acquire format data including a plurality of measurement items;
a measurement data acquisition component configured to acquire the measurement data relating to the plurality of measurement items from the electronic apparatuses relating to measurement of the plurality of measurement items based on communication with the electronic apparatuses;
a generation component configured to generate first measurement result data including the plurality of measurement items and including first biological information based on the measurement data, and configured to generate second measurement result data including the plurality of measurement items and including second biological information based on the measurement data, the second biological information being at least partially different than the first biological information,
wherein the generation component is further configured to classify, based on user information corresponding to the biological body, the first measurement result data using a first set of specified hierarchy-based classes and to classify, based on the user information, the second measurement result data using a second set of specified hierarchy-based classes that are different form the first set of specified hierarchy-based classes; and
a record processing component configured to record the first measurement result data and the second measurement result data.

10. The image processing system according to claim 9, further comprising a user information acquisition component configured to acquire the user information including a biological information history, wherein the generation component generates time-series data of biological information based on the biological information history in the user information and the biological information, and the measurement result data includes the time-series data.

11. The image processing system according to claim 9, further comprising:

an abnormality detection component configured to detect a plurality of different abnormalities of the biological information based on reference values of biological information; and an output component configured to output a set of notifications in response to the detection of the abnormalities by the abnormality detection component, wherein the output component outputs a first notification, of the set of notifications, to a first destination institution and a second notification, of the set of notifications, to a second destination institution that is different from the first destination institution.

12. The image processing system according to claim 11, wherein the measurement result data includes abnormality information representing the abnormality.

13. The image processing system according to claim 9, wherein the electronic apparatus comprises a sensor configured to acquire biological data.

14. The image processing system according to claim 9, wherein the measurement item is a medical measurement item.

15. The image processing system according to claim 9, wherein the measurement data acquisition component communicates wirelessly with the electronic apparatus.

16. The image processing system according to claim 11, wherein the abnormality comprises a value exceeding a reference value by a predetermined range or a value falling below the reference value by the predetermined range.

17. An image processing method, comprising:

acquiring format data including a plurality of measurement items;

acquiring measurement data of a biological body relating to the plurality of measurement items from one or more electronic apparatuses relating to measurement of the plurality of measurement items based on communication with the electronic apparatuses;

generating first measurement result data including the plurality of measurement items and including first biological information based on the measurement data, and generating second measurement result data including the plurality of measurement items and including second biological information based on the measurement data, the second biological information being at least partially different than the first biological information, wherein the generation component is further configured to classify, based on user information corresponding to the biological body, the first measurement result data using a first set of specified hierarchy-based classes and to classify, based on the user information, the second measurement result data using a second set of specified hierarchy-based classes that are different form the first set of specified hierarchy-based classes; and recording the first measurement result data and the second measurement result data.

18. The image processing method according to claim 17, further comprising:

acquiring the user information including a biological information history; and generating time-series data of biological information based on the biological information history in the user information and the biological information, wherein the measurement result data includes the time-series data.

19. The image processing method according to claim 17, further comprising:

detecting a plurality of different abnormalities of the biological information based on a reference value of biological information; and outputting a set of notifications in response to detecting the abnormalities, comprising outputting a first notification, of the set of notifications, to a first destination institution and outputting a second notification, of the set of notifications, to a second destination institution that is different from the first destination institution.

20. The image processing method according to claim 19, wherein the measurement result data includes abnormality information representing the abnormality.

* * * * *